(12) United States Patent
Kotoku et al.

(10) Patent No.: US 10,123,698 B2
(45) Date of Patent: Nov. 13, 2018

(54) OPHTHALMIC APPARATUS, INFORMATION PROCESSING METHOD, AND STORAGE MEDIUM

(71) Applicant: CANON KABUSHIKI KAISHA, Tokyo (JP)

(72) Inventors: Masashi Kotoku, Yokohama (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/245,995

(22) Filed: Aug. 24, 2016

(65) Prior Publication Data

US 2017/0055830 A1   Mar. 2, 2017

(30) Foreign Application Priority Data

Aug. 27, 2015 (JP) ................. 2015-168287

(51) Int. Cl.
| | |
|---|---|
| *G06K 9/00* | (2006.01) |
| *A61B 3/12* | (2006.01) |
| *A61B 3/10* | (2006.01) |
| *A61B 3/00* | (2006.01) |

(52) U.S. Cl.
CPC .......... *A61B 3/1233* (2013.01); *A61B 3/0025* (2013.01); *A61B 3/0058* (2013.01); *A61B 3/102* (2013.01); *A61B 3/1241* (2013.01)

(58) Field of Classification Search
CPC .......................... A61B 3/1241; A61B 3/1233
See application file for complete search history.

(56) References Cited

U.S. PATENT DOCUMENTS

| | | | |
|---|---|---|---|
| 2013/0182219 A1* | 7/2013 | Numajiri ............... | A61B 3/113 351/206 |
| 2014/0221827 A1 | 8/2014 | Motaghiannezam et al. | |
| 2015/0201829 A1* | 7/2015 | Yang .................. | G01N 21/4795 382/131 |
| 2015/0374228 A1* | 12/2015 | Satake ................. | G06T 7/0016 351/206 |
| 2016/0278627 A1* | 9/2016 | Huang ................. | A61B 3/0025 |
| 2017/0164825 A1* | 6/2017 | Chen ..................... | A61B 3/102 |

\* cited by examiner

*Primary Examiner* — Oneal R Mistry
(74) *Attorney, Agent, or Firm* — Canon U.S.A., Inc. IP Division

(57) ABSTRACT

An ophthalmic apparatus includes a generation unit configured to generate 3D blood vessel data indicating a blood vessel in a fundus based on a plurality of tomographic image data indicating cross sections of the fundus, a boundary obtaining unit configured to obtain layer boundary data indicating at least one layer boundary based on 3D tomographic image data including the plurality of tomographic image data indicating the cross sections of the fundus, and a determination unit configured to determine a blood vessel intersecting with the layer boundary by comparing the 3D blood vessel data with the layer boundary data.

14 Claims, 8 Drawing Sheets

OPHTHALMIC APPARATUS, INFORMATION PROCESSING METHOD, AND STORAGE MEDIUM

BACKGROUND OF THE INVENTION

Field of the Invention

The disclosed technique relates to an ophthalmic apparatus, an information processing method, and a storage medium.

Description of the Related Art

As a method for obtaining a tomographic image of a measurement object, such as a living body, in a non-destructive manner and a non-invasive manner, optical coherence tomography (OCT) is used in practice. The OCT is widely used in ophthalmic diagnoses in particular.

In the OCT, light reflected by the measurement object and light reflected by a reference mirror interfere with each other and an intensity of a resultant interference light is analyzed so that a tomographic image of the measurement object is obtained. Examples of such a light interference tomographic image obtaining apparatus include spectral domain optical coherence tomography (SD-OCT) which divides interference light and which replaces depth information by frequency information to be obtained and swept source optical coherence tomography (SS-OCT) which divides wavelength first before outputting light. Note that, the SD-OCT and the SS-OCT are collectively referred to as Fourier domain optical coherence tomography (FD-OCT).

In recent years, an angiography method using the FD-OCT has been proposed which is referred to as "OCT angiography". U.S. Patent Application Publication No. 2014/221827 discloses OCT angiography which determines variation of logarithmic intensity of an interference signal as a motion contrast feature value and generates an image of the motion contrast feature value.

However, U.S. Patent Application Publication No. 2014/221827 does not disclose a method for specifying a blood vessel having a possibility of a new blood vessel in an image of blood vessels obtained by imaging the motion contrast feature value.

SUMMARY OF THE INVENTION

A disclosed ophthalmic apparatus includes a generation unit configured to generate 3D blood vessel data indicating a blood vessel in a fundus based on a plurality of tomographic image data indicating cross sections of the fundus, a boundary obtaining unit configured to obtain layer boundary data indicating at least one layer boundary based on 3D tomographic image data including the plurality of tomographic image data indicating the cross sections of the fundus, and a determination unit configured to determine a blood vessel intersecting with the layer boundary by comparing the 3D blood vessel data with the layer boundary data.

Further features of the present invention will become apparent from the following description of exemplary embodiments with reference to the attached drawings.

DESCRIPTION OF THE EMBODIMENTS

Hereinafter, an image generation apparatus according to an embodiment will be described with reference to the accompanying drawings. Note that configurations in embodiments below are merely examples, and the present invention is not limited to the embodiments.

First Embodiment

Configuration of Entire Imaging Apparatus

A first embodiment will be described hereinafter with reference to the accompanying drawings.

Figure 1:
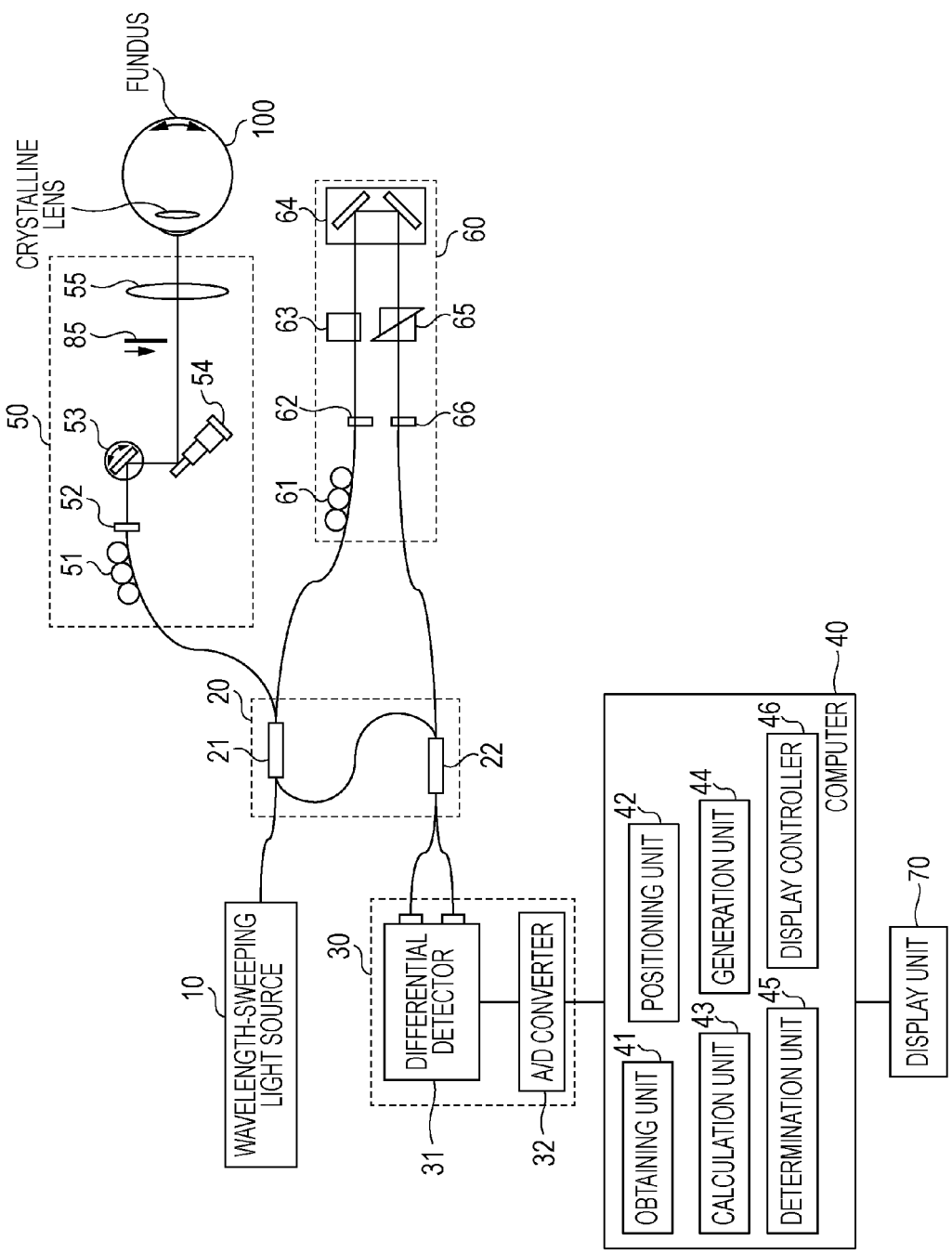
FIG. 1 is a diagram illustrating an entire configuration of an imaging apparatus.

FIG. 1 is a diagram illustrating a configuration of an imaging apparatus (an OCT apparatus) employing optical coherence tomography according to this embodiment. Although a configuration of the SS-OCT is illustrated in FIG. 1, the same effect may be realized by an OCT apparatus employing other methods.

This OCT apparatus (an ophthalmic apparatus) includes a wavelength-sweeping light source 10, an optical signal branching/multiplexing unit 20, an interference light detection unit 30, a computer 40 (the ophthalmic apparatus) which obtains information on a retina of a human eye 100, a measurement arm 50, and a reference arm 60. The computer 40 includes a central arithmetic operation unit (CPU) and a storage device. The storage unit includes memories (a RAM and a ROM) and a mass storage (HDD), for example. A portion of the storage device or the entire storage device may be disposed outside the computer 40. The wavelength-sweeping light source 10 emits light having a wavelength in a range from 980 nm to 1100 nm in a frequency of 100 kHz (an A scan rate), for example. Here, the wavelength and the frequency are merely examples, and the present invention is not limited to the values described above. Similarly, in the embodiments described below, described numerical values are merely examples, and the present invention is not limited to the described numerical values.

Note that, although a human eye (a fundus) is set as an object 100 in this embodiment, the present invention is not limited to this, and the present invention may be applied to a skin, for example. Furthermore, although the fundus is set as an imaging target in this embodiment, an anterior eye may be set as an imaging target.

The optical signal branching/multiplexing unit 20 includes couplers 21 and 22. The coupler 21 divides light emitted from the light source 10 into irradiation light to be emitted to a fundus and reference light. The irradiation light is emitted to the human eye 100 through the measurement arm 50. Specifically, the irradiation light which enters the measurement arm 50 is output from a collimator 52 as spatial light after a polarization state of the irradiation light is adjusted by a polarized light controller 51. Thereafter, the irradiation light is emitted to the fundus of the human eye 100 through an x-axis scanner 53, a y-axis scanner 54, and a focus lens 55. The x-axis scanner 53 and the y-axis scanner 54 are included in a scanning unit having a function of scanning a fundus with irradiation light. The scanning unit changes a position of irradiation with the irradiation light on the fundus. Here, a process of obtaining information on a point of the human eye 100 in a depth direction is referred to as "A scan". Furthermore, a process of obtaining a 2D tomographic image along a direction orthogonal to the direction of the A scan is referred to as "B scan", and a process of obtaining a 2D tomographic image along a direction vertical to the 2D tomographic image of the B scan is referred to as "C scan".

Note that the x-axis scanner 53 and the y-axis scanner 54 are configured by mirrors having rotation axes which are orthogonal to each other. The x-axis scanner 53 performs scanning in an x direction and the y-axis scanner 54 performs scanning in a y direction. The x direction and the y direction are vertical to an eye axis direction of an eyeball and are vertical to each other. Furthermore, directions of line scan, such as the B scan and the C scan, may not coincide with the x direction or the y direction. Therefore, line scan directions of the B scan and the C scan may be appropriately determined in accordance with a 2D tomographic image to be captured or a 3D tomographic image to be captured.

Reflection light from the fundus is incident on the coupler 22 through the coupler 21 after passing through the same path including the focus lens 55 again. Note that, if a measurement is performed in a state in which a shutter 85 is closed, a measurement of a background (noise floor) may be performed while the reflection light from the human eye 100 is cut.

On the other hand, the reference light is incident on the coupler 22 through the reference arm 60. Specifically, the reference light which enters the reference arm 60 is output from a collimator 62 as spatial light after a polarization state of the reference light is adjusted by a polarized light controller 61. Thereafter, the reference light is incident on an optical fiber through a dispersion compensation glass 63, an optical path length control optical system 64, a dispersion control prism pair 65, and a collimator lens 66, emitted from the reference arm 60, and further incident on the coupler 22.

Figure 7:
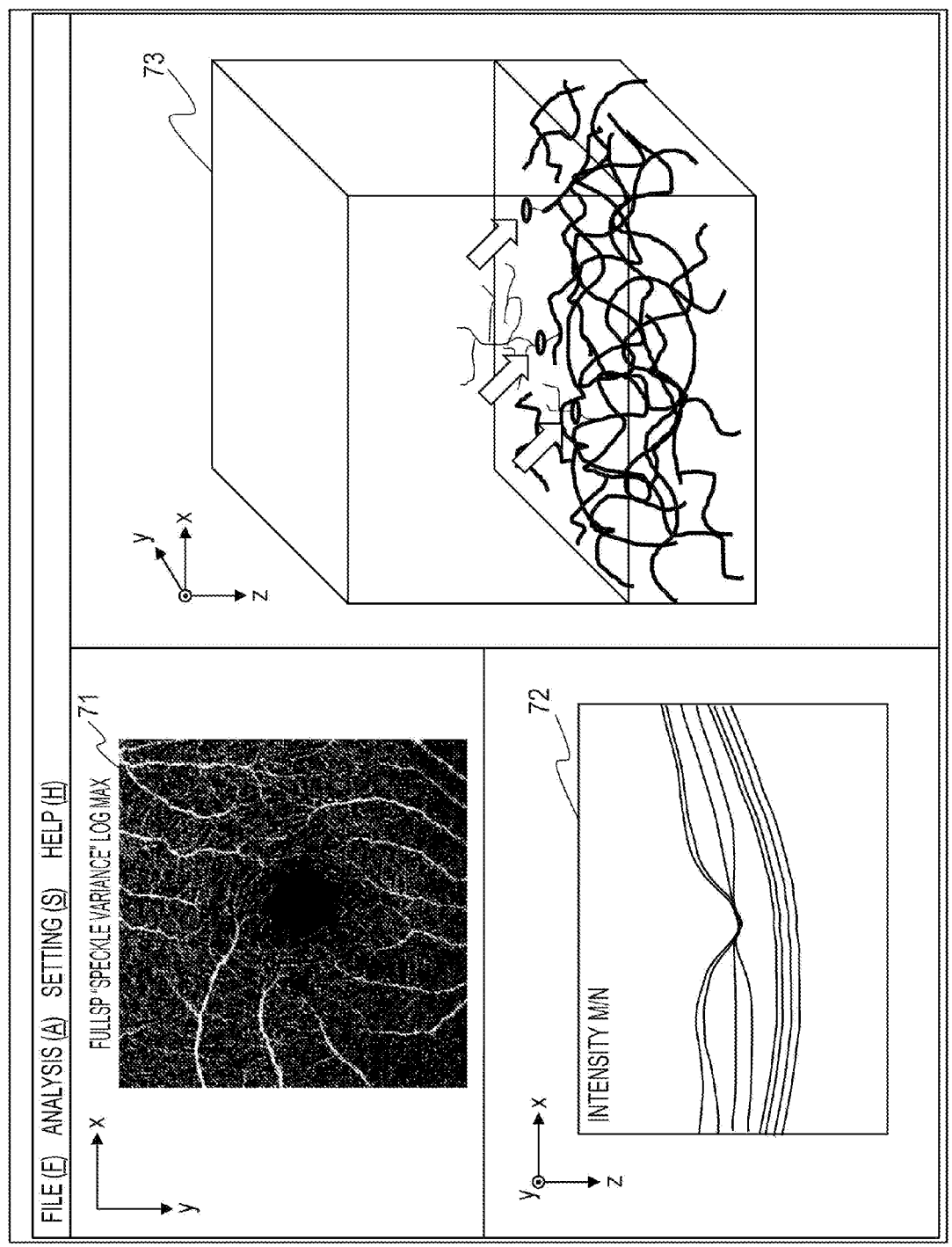
FIG. 7 is a diagram illustrating a display screen of a display unit.

In the coupler 22, the reflection light of the human eye 100 transmitted through the measurement arm 50 and the reference light transmitted through the reference arm 60 interfere with each other. Resultant interference light is detected by the detection unit 30. The detection unit 30 includes a differential detector 31 and an A/D converter 32. First, the differential detector 31 of the detection unit 30 detects the interference light divided by the coupler 22. Then the A/D converter 32 converts an OCT interference signal (hereinafter simply referred to as an "interference signal" where appropriate) which has been converted into an electric signal by the differential detector 31 into a digital signal. Here, the differential detector 31 performs sampling of the interference light at even wavenumber interval in accordance with a k clock signal generated by a clock generator incorporated in the wavelength-sweeping light source 10. The digital signal output from the A/D converter 32 is supplied to the computer 40. Subsequently, the computer 40 performs signal processing on the interference signal which has been converted into the digital signal so as to calculate an OCT angiography image. FIG. 7 is a diagram illustrating the OCT angiography image.

A CPU included in the computer 40 executes various processes. Specifically, the CPU executes programs stored in a storage device, not illustrated, so as to function as an obtaining unit 41, a positioning unit 42, a calculation unit 43, a generation unit 44, a determination unit 45, and a display controller 46. The computer 40 includes at least one CPU and at least one storage device. Specifically, at least one processing unit (the CPU) and at least one storage device (a ROM, a RAM, or the like) are connected to each other, and the computer 40 functions as the units described above when the at least one processing unit executes programs stored in the at least one storage device. Note that the processing unit is not limited to the CPU and may be a field-programmable gate array (FPGA) or the like. Furthermore, the computer 40 may be an apparatus which is integrated with a display unit 70 and which is portable by a user (a tablet). In this case, the display unit 70 may have a touch panel function which accepts various user operations performed on a touch panel.

The obtaining unit 41 obtains an output from the A/D converter 32. Specifically, the obtaining unit 41 obtains the digital signal of the interference light obtained from the measurement light which is returned from an eye to be inspected and which is used for scanning on the eye to be inspected and the reference light which interfere with each other. The obtaining unit 41 further obtains a tomographic image by performing Fourier transform on the digital signal of the interference light (the interference signal). Specifically, the obtaining unit 41 obtains an OCT complex signal formed by a phase and amplitude by performing fast Fourier transform (FFT) on the interference signal. Note that a maximum entropy method may be used as frequency analysis. The obtaining unit 41 further obtains a tomographic image indicating intensity (hereinafter simply referred to as a "tomographic image" where appropriate) by calculating square of an absolute value of the OCT complex signal so as to obtain a signal intensity (intensity). This tomographic image corresponds to an example of tomographic data indicating a layer of the fundus of the eye to be inspected. Specifically, in a case where the fundus of the eye to be inspected is scanned a plurality of times using the measurement light in substantially the same position, the obtaining unit 41 obtains a plurality of tomographic data indicating layers of the subject in substantially the same position. Note that the plurality of tomographic data is obtained using the measurement light used in scanning operations performed in different timings. Furthermore, in a case where scanning is performed on a plurality of positions of the fundus using the measurement light, the obtaining unit 41 obtains a plurality of tomographic data in the plurality of positions. Specifically, the obtaining unit 41 corresponds to an example of first and second obtaining units.

Note that the obtaining unit 41 also functions as a unit which controls the various units included in the OCT apparatus, such as the x-axis scanner 53 and the y-axis scanner 54.

The positioning unit 42 performs positioning of a plurality of tomographic images. In this embodiment, the positioning unit 42 performs positioning of a plurality of tomographic images obtained by performing scanning a plurality of times on the fundus of the eye to be inspected using the measurement light in substantially the same position. More specifically, the positioning unit 42 performs positioning of a plurality of tomographic data before the calculation unit 43 calculates a motion contrast value.

The positioning of tomographic images may be realized by one of general methods. The positioning unit 42 performs positioning of the plurality of tomographic images such that the correlation among the tomographic images becomes maximum, for example. Note that the positioning is not required in a case where the subject is not moved unlike an eye. Furthermore, the positioning is not required if a high tracing function is provided even in a case where the subject is an eye. That is, positioning of tomographic images by the positioning unit 42 is not essential.

The calculation unit 43 calculates a motion contrast feature value (hereinafter referred to as a "motion contrast value" where appropriate). Here, the term "motion contrast" indicates contrast between a flowing tissue (such as a blood) and a nonflowing tissue, and a feature value representing the motion contrast is defined as the "motion contrast feature value".

The motion contrast feature value is calculated based on a change of data of a plurality of tomographic images obtained by performing scanning a plurality of time using the measurement light in substantially the same position. For example, the calculation unit 43 calculates dispersion of signal intensities (luminance) of the plurality of tomographic images which have been subjected to the positioning as the motion contrast feature value. More specifically, dispersion of signal intensities in positions corresponding to the plurality of tomographic images which have been subjected to the positioning is calculated as the motion contrast feature value. For example, signal intensity of an image of a blood vessel at a certain time point is different from signal intensity of an image of the blood vessel at another time point, and therefore, a dispersion value of a portion corresponding to the blood vessel is larger than that of a portion in which flowing, such as a blood flow, is not detected. Specifically, the motion contrast value becomes large as a change in the subject among the plurality of tomographic data becomes large. Accordingly, the motion contrast may be represented by generating an image based on the dispersion value. Note that the motion contrast feature value is not limited to the dispersion value, and may be standard deviation, a difference value, a decorrelation value, or a correlation value. Note that, although the calculation unit 43 uses the dispersion of signal intensities or the like, the motion contrast feature value may be calculated using dispersion of phases.

Furthermore, the calculation unit 43 generates an averaging image by calculating an average value of the plurality of tomographic images which have been subjected to the positioning. The averaging image is a tomographic image obtained by averaging the signal intensities of the plurality of tomographic images. The averaging image may be referred to as an "intensity averaging image". The calculation unit 43 compares a signal intensity of the averaging image with a threshold value. In a case where a signal intensity of a certain position of the averaging image is smaller than the threshold value, the calculation unit 43 sets a motion contrast feature value obtained based on dispersion or the like in the certain position of the averaging image as a value different from a feature value indicating a blood vessel. In the case where the signal intensity of the averaging image is lower than the threshold value, for example, the calculation unit 43 sets a motion contrast feature value obtained based on the dispersion or the like as 0. Specifically, in a case where a representative value indicating the signal intensity is lower than the threshold value, the calculation unit 43 sets a motion contrast value as a value smaller than a motion contrast value obtained in a case where the representative value indicating the signal intensity is equal to or higher than the threshold value. Note that the calculation unit 43 may compare the signal intensity of the averaging image with the threshold value before calculating the dispersion of the signal intensities of the plurality of tomographic images as the motion contrast feature value. In a case where the signal intensity of the averaging image is lower than the threshold value, for example, the calculation unit 43 calculates a motion contrast feature value of 0 whereas in a case where the signal intensity of the averaging image is equal to or higher than the threshold value, the calculation unit 43 calculates the dispersion of the signal intensities of the plurality of tomographic images as the motion contrast feature value.

Here, the feature value of 0 denotes a black portion denoted by a reference numeral 71 in a 2D blood vessel image illustrated in FIG. 7. Note that the motion contrast feature value may not be 0 flat and may be a value near 0. On the other hand, in the case where the signal intensity of the averaging image is equal to or higher than the threshold value, the calculation unit 43 maintains the motion contrast feature value obtained based on the dispersion and the like. Specifically, the calculation unit 43 calculates the motion contrast value based on the plurality of tomographic image data and calculates again the motion contrast value based on a result of comparison between the representative value indicating the signal intensity and the threshold value.

Although the signal intensity of the averaging image (an average value of the signal intensities) is used as a target of the comparison with the threshold value, the highest value, the lowest value, a median value, or the like of the signal intensities in the positions corresponding to the plurality of tomographic images may be used as the representative value. Furthermore, instead of the comparison between the signal intensities obtained from the plurality of tomographic images with the threshold value, the calculation unit 43 may compare a signal intensity of one tomographic image with the threshold value and control the motion contrast feature value.

The generation unit 44 generates 3D blood vessel information (3D blood vessel data) based on the motion contrast feature value. Specifically, the generation unit 44 corresponds to an example of a generation unit which generates 3D blood vessel data indicating a blood vessel in the fundus based on the plurality of tomographic image data indicating layers of the fundus.

Specifically, the generation unit 44 compares the motion contrast feature value with a threshold value so as to perform the region dividing process of distinguishing a blood vessel region from other regions. Furthermore, the generation unit 44 may perform a smoothing process on the motion contrast feature value before executing the region dividing process. The smoothing process will be described in detail later. Note that the 3D blood vessel information includes a 3D blood vessel image. Specifically, the 3D blood vessel information indicates the 3D blood vessel image.

Furthermore, the generation unit 44 may generate 2D blood vessel information (2D blood vessel data) by performing projection or integration on the 3D blood vessel information in a depth range in an arbitrary retina direction. The 2D blood vessel information includes a 2D blood vessel image (an en-face blood vessel image). Specifically, the 2D blood vessel information indicates a 2D blood vessel image. The reference numeral 71 of FIG. 7 indicates an example of the 2D blood vessel image.

Furthermore, the generation unit 44 may extract the depth range in the arbitrary retina direction from the 3D blood vessel information so as to generate partial 3D blood vessel information.

Note that the depth range in the arbitrary retina direction may be set by an examiner (an operator). For example, candidates of a selectable layer, such as layers from IS/OS to RPE and layers from RPE to BM are displayed in the display unit 70. Among the displayed candidates of the layer, the examiner selects a certain layer. The generation unit 44 may perform integration on the layer selected by the examiner in the retina depth direction so as to generate 2D blood vessel information or partial 3D blood vessel information.

Furthermore, the generation unit 44 obtains layer boundary data indicating at least one layer boundary from the 3D tomographic image data including the plurality of tomographic image data. Specifically, the generation unit 44 corresponds to an example of a boundary obtaining unit which obtains layer boundary data indicating at least one layer boundary based on the 3D tomographic image data including the plurality of tomographic image data indicating layers of the fundus. The layer boundary data is 3D data, for example. A method for detecting a layer boundary will be described in detail later.

Note that, in this embodiment, the 3D layer boundary data and the 3D blood vessel data are obtained based on the same tomographic image data. Specifically, the generation unit 44 which is an example of the boundary obtaining unit obtains layer boundary data indicating at least one layer boundary based on the 3D tomographic image data including the plurality of tomographic image data indicating the layers of the fundus used in the generation of the 3D blood vessel data.

The determination unit 45 determines a blood vessel which intersects with the layer boundary by comparing the 3D layer boundary data with the layer boundary data. Furthermore, the determination unit 45 may determine a blood vessel included in a certain range from the layer boundary by comparing the 3D layer boundary data with the layer boundary data. Note that the determination unit 45 extracts a blood vessel which is seen to be a new blood vessel. The process of the determination unit 45 will be described in detail later.

The display controller 46 displays various information in the display unit 70. Specifically, the display controller 46 displays the 3D blood vessel image indicated by the 3D blood vessel information generated by the generation unit 44 in the display unit 70. Furthermore, the display controller 46 displays the blood vessel determined by the determination unit 45 in the display unit 70 in a state in which the determined blood vessel is distinguished from other blood vessels. The display controller 46 may display a 2D blood vessel image in the display unit 70. Moreover, the display controller 46 may display the blood vessel determined by the determination unit 45 included in the 2D blood vessel image in the display unit 70 in a state in which the determined blood vessel is distinguished from other blood vessels. The display controller 46 may display at least one of the 3D blood vessel image and the 2D blood vessel image in the display unit 70. Specifically, the display controller 46 corresponds to an example of a display controller which displays at least one of the 3D blood vessel image indicated by the 3D blood vessel data and the 2D blood vessel image obtained by performing the integration on the 3D blood vessel data in the fundus depth direction in the display unit and which displays the blood vessel determined by the determination unit in the display unit in a state in which the determined blood vessel is distinguished from other blood vessels. Control performed by the display controller 46 will be described in detail later.

A procedure of signal processing performed by the computer 40 will be described in detail later.

The display unit 70 displays various information under control of the display controller 46. The display unit 70 is a liquid crystal display, for example. Furthermore, the display unit 70 displays an OCT angiography image obtained as a result of the signal processing described above.

Scanning Pattern

Next, a scanning pattern of this embodiment will be described with reference to FIG. 2.

In the OCT angiography, a change of the interference signal with time due to blood flow is to be measured, and therefore, a plurality of interference signals repeatedly measured in substantially the same portion at least twice are required. In FIG. 2, a Z axis denotes an axial direction of the irradiation light emitted to the human eye 100 (a depth direction), and X and Y axes form a plane orthogonal to the Z axis, that is, the X and Y axes correspond to a fundus plane direction.

Figure 2:
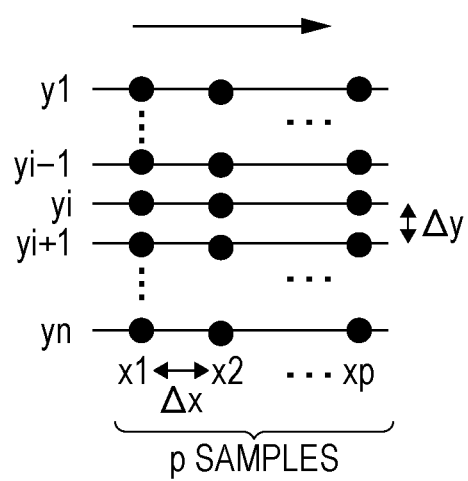
FIG. 2 is a diagram illustrating a scanning pattern.

In FIG. 2, y1 to yn denote B scan in different Y positions, and n denotes the number of samples in a y scan direction. Furthermore, x1 to xp denote sample positions in an X scan direction, and p denotes the number of samples in the X scan direction included in the B scan. Moreover, Δx denotes an interval between adjacent X positions (an x pitch), and Δy denotes an interval between adjacent Y positions (a y pitch). In addition, m denotes the number of times the measurement is repeatedly performed by the B scan in substantially the same portion. Here, an initial position (x1, y1) may be arbitrarily set by the computer 40.

In this embodiment, the OCT apparatus repeatedly performs the B scan m times in substantially the same portion, and performs a scan method of moving to y positions in n portions. Note that the repeat scan method may be a scan method of repeatedly performing A scan in substantially the same portion and moving to a next position for forming the B scan.

Here, if the number m of times the repeat scan is performed is large, the number of times the measurement is performed in the same portion is increased, and therefore, detection accuracy of blood flow is improved. However, a long period of time is required for the scanning, and therefore, there arise problems in that motion artifact is generated in an image due to a motion of an eye (an involuntary eye movement) during the scanning and a burden for an examinee is increased. In this embodiment, 4 is set to m taking balance between the number m of times the repeat scan is performed and the number of times the scanning is performed in the same position into consideration. Note that m may be freely changed in accordance with an A scan speed of the OCT apparatus and a moving amount of the human eye 100. Specifically, the number of times the repeat scan is performed is not limited to the value described above.

Furthermore, an image size in the x and y directions is determined by p×n. If the image size in the x and y directions is large, a large range may be scanned with the same measurement pitch. However, a long period of time is required for the scanning and the problems in the motion artifact and a burden for a patient arise. In this embodiment, 300 is set to n and p taking balance between the image size and the scanning time into consideration. Note that values of n and p above may be appropriately changed. Specifically, the image size is not limited to the value described above.

Furthermore, in this embodiment, an x pitch and a y pitch are determined as a half of a beam spot diameter of the irradiation light on the fundus, that is, 10 μm. Since the x pitch and the y pitch are determined as a half of the beam spot diameter on the fundus, a high definition image may be generated. Even if the x pitch and the y pitch are smaller than a half of the beam spot diameter on the fundus, definition of a generated image is barely improved.

On the other hand, if the x pitch and the y pitch are larger than a half of the beam spot diameter on the fundus, although definition is degraded, an image in a large range may be obtained. The x pitch and the y pitch may be freely changed in accordance with a clinical demand.

A scan range of this embodiment is determined as follows: 3 mm (p×Δx) in an x direction and 3 mm (n×Δy) in a y direction.

Procedure of Obtainment of Interference Signal

Next, an example of a procedure of an obtainment of an interference signal according to this embodiment will be described with reference to FIG. 3.

In step S109, the obtaining unit 41 assigns 1 to an index i of a position yi illustrated in FIG. 2. Thereafter, in step S110, the obtaining unit 41 controls a driving mechanism, not illustrated, so as to move scanning positions of the x-axis scanner 53 and the y-axis scanner 54 to a coordinate (x1, yi) of FIG. 2. In step S119, the obtaining unit 41 initializes an index j of the number of times repeat measurement is performed in the B scan to 1.

In step S120, the x-axis scanner 53 and the y-axis scanner 54 perform j-th B scan of the repeat measurement. Note that a range of the B scan is (x1, yi) to (xp, yi). Here, the wavelength-sweeping light source 10 emits light in an A scan rate of 100 kHz, and the number p of samples in the x scan direction of the B scan is 300, for example. Accordingly, a net B scan time (Δtb) is represented by Expression 1 below.

$$\Delta tb = (1/100 \text{ kHz}) \times 300 = 3 \text{ ms} \qquad \text{Expression 1}$$

Furthermore, as represented by Expression 2, a time interval of the repeat measurement is a sum of the net B scan time Δtb and a preparation time Δtp of the x-axis scanner 53. The preparation time Δtp is a period of time in which scan positions of the x-axis scanner 53 and the y-axis scanner 54 are adjusted, for example. Assuming that Δtp is 1 ms, Expression 2 is obtained.

$$\Delta t = \Delta tb + \Delta tp = 4 \text{ ms} \qquad \text{Expression 2}$$

Furthermore, an entire measurement time tm is represented by Expression 3 using the number m of times repetition is performed and the number n of samples in the y scan direction.

$$tm = \Delta t \cdot m \cdot n = (\Delta tb + \Delta tp) \cdot m \cdot n \qquad \text{Expression 3}$$

Since m is 4 and y is 300 in this embodiment, the entire measurement time tm is 3.6 s.

Here, as the B scan time Δtb and a time interval Δt of the repeat measurement are small, influence of a motion of the human eye 100 is small and bulk motion noise is small. On the other hand, the time interval Δt is long, positional reproducibility is degraded due to a motion of the human eye 100, and accordingly, the bulk motion noise is increased. Furthermore, a period of time required for the measurement is increased, and a burden for the patient is increased. Here, the bulk motion means a motion of the eye to be inspected, and the bulk motion noise means noise generated due to a motion of the eye to be inspected.

Furthermore, if the time interval Δt of the repeat measurement is too small, a period of time required for detection of a blood flow is short, and accordingly, blood flow detection sensitivity is degraded.

Therefore, tm, Δt, n, p, Δtb, and Δtp are preferably selected taking these elements into consideration. Note that, to enhance the positional reproducibility of the repeat measurement, the x-axis scanner 53 and the y-axis scanner 54 may perform the B scan while tracing the human eye 100.

In step S130, the differential detector 31 detects the interference light for each A scan, and the interference light is converted into a digital signal (an interference signal) through the A/D converter 32. The obtaining unit 41 obtains the interference signal from the A/D converter 32 and stores the interference signal in a storage unit, not illustrated. The obtaining unit 41 obtains p A scan signals per one B scan. The p A scan signals corresponds to one B scan signal.

In step S139, the obtaining unit 41 increments the index j of the number of times the repeat measurement of the B scan is performed.

In step S140, the obtaining unit 41 determines whether the index j of the number of times the repeat measurement is performed is larger than a predetermined repeat number m. Specifically, the obtaining unit 41 determines whether the B scan is repeatedly performed m times in the position yi. When the determination is negative in step S140, the process returns to step S120 where the B scan measurement in the same position is performed again. When the determination is affirmative in step S140, the process proceeds to step S149.

In step S149, the obtaining unit 41 increments the index i of the position yi.

In step S150, the obtaining unit 41 determines whether the index i of the position yi is larger than the predetermined number n of measurement positions, that is, whether the B scan has been performed in all Y positions in n portions. When the determination is negative, the process returns to step S110 so that an operation of performing the measurement in a next measurement position is performed again. On the other hand, when the determination is affirmative, the process proceeds to step S160.

In step S160, the obtaining unit 41 obtains background data. The obtaining unit 41 controls a driving unit, not illustrated, so as to perform the A scan 100 times in a state in which the shutter 85 is closed, averages 100 A scan signals, and stores a resultant value in a storage unit. Note that the number of times A scan is performed for obtaining the background data is not limited to 100.

The obtaining unit 41 may obtain the plurality of interference signals obtained by performing the repeat measurement at least twice in substantially the same portion and the background data.

Signal Processing Procedure

Next, an example of the signal processing procedure (an information processing method) according to this embodiment will be described with reference to FIG. 4.

Figure 4:
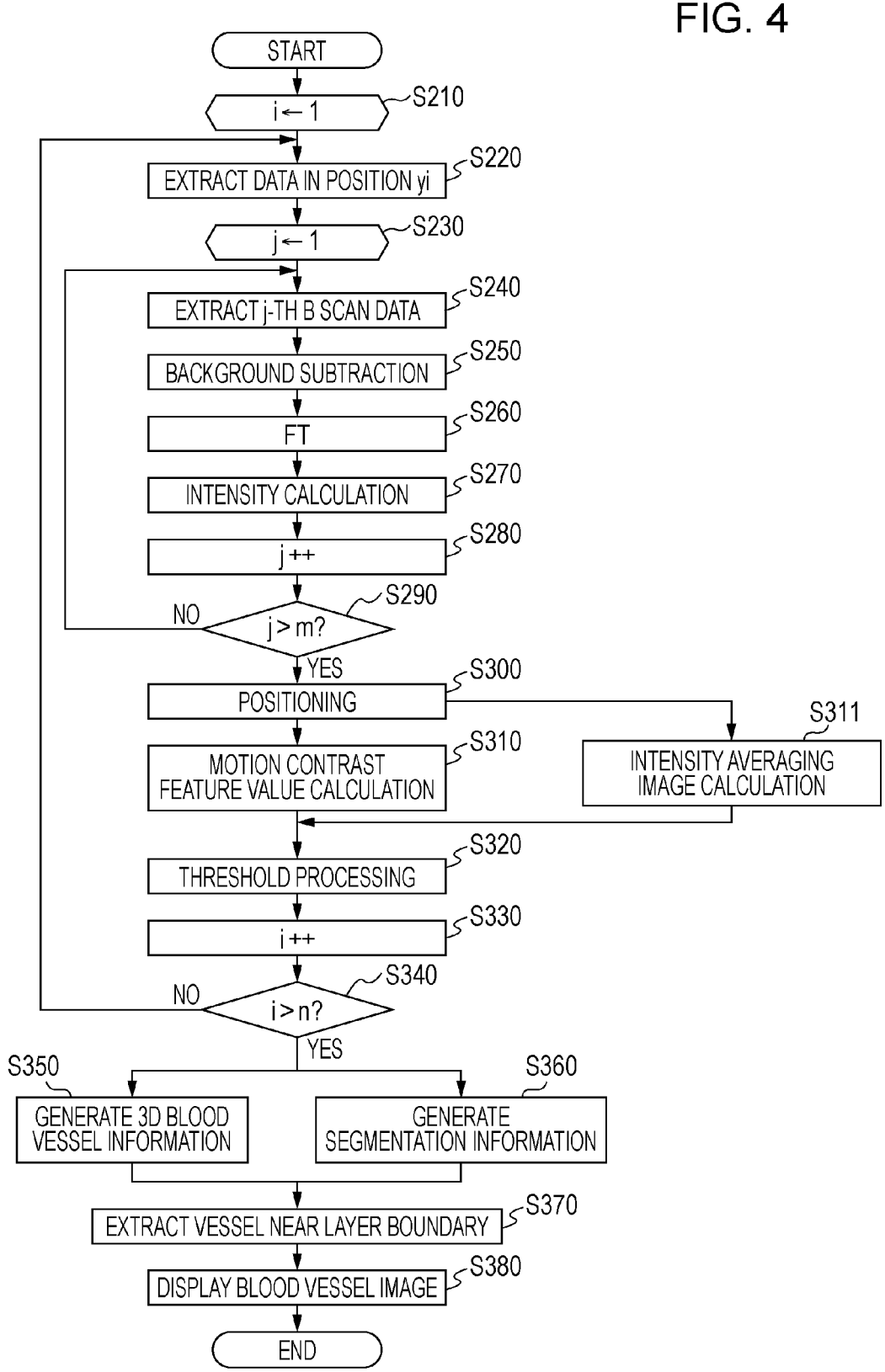
FIG. 4 is a flowchart illustrating a procedure of signal processing.

FIG. 4 is a flowchart illustrating a flow from an obtainment of interference signals to display of a 3D blood vessel image.

In this embodiment, a motion contrast feature value is required to be calculated to generate an OCT angiography image.

In step S210 of FIG. 4, the obtaining unit 41 sets the index i of the position yi in the y direction as 1. In step S220, the obtaining unit 41 extracts (m) B scan interference signals obtained by the B scan repeatedly performed from the interference signals obtained by the process illustrated in FIG. 3 stored in the storage unit. Specifically, the obtaining unit 41 reads a plurality of B scan interference signals obtained by the repeat B scan in the position yi from the storage unit.

In step S230, the obtaining unit 41 sets the index j of the repeat B scan as 1.

In step S240, the obtaining unit 41 extracts a j-th B scan interference signal from the m B scan interference signals.

Figure 3:
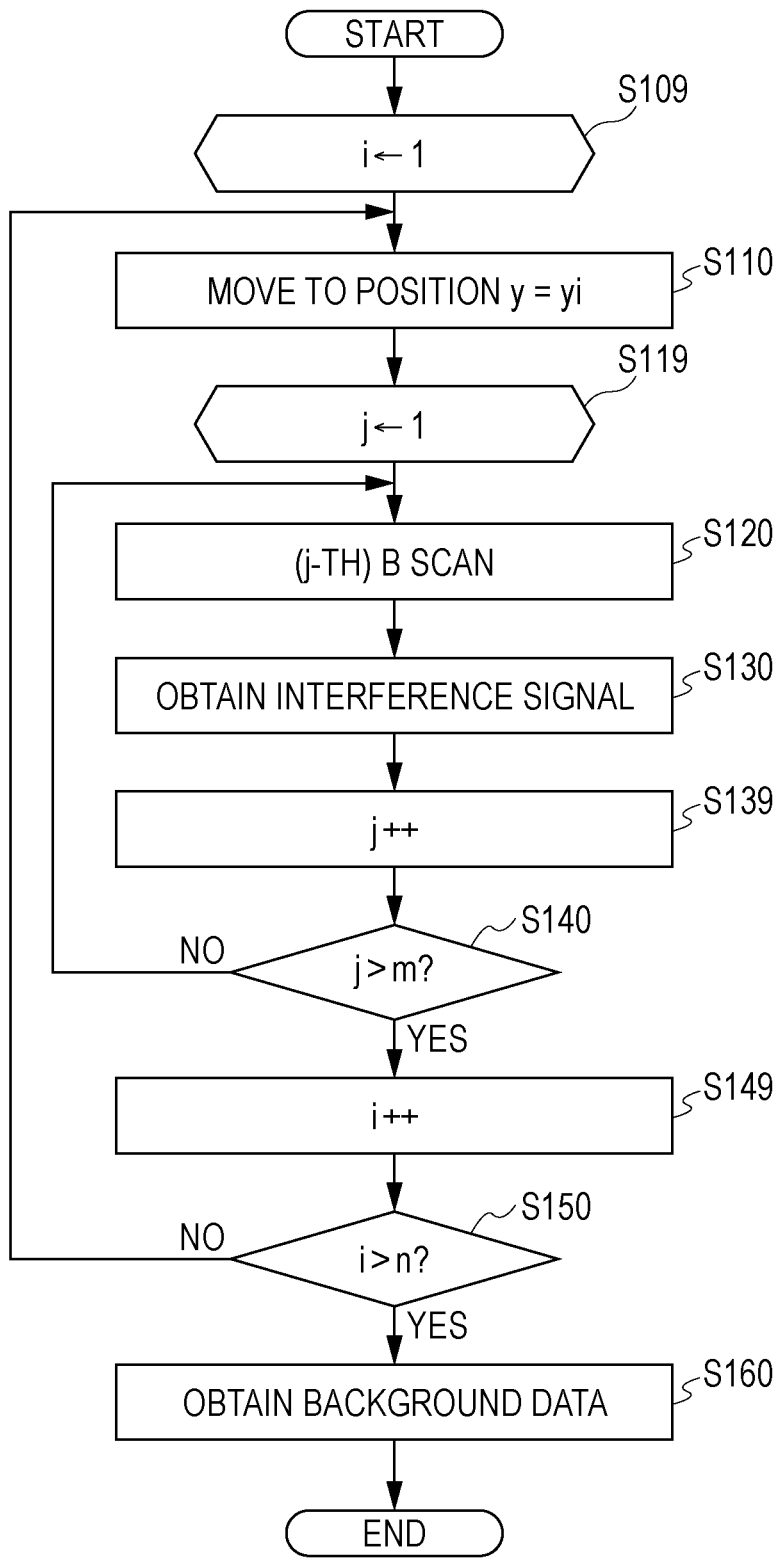
FIG. 3 is a flowchart illustrating a procedure of an obtainment of an interference signal.

In step S250, the computer 40 subtracts the background data obtained in step S160 of FIG. 3 from the B scan interference signal obtained in step S240.

In step S260, the obtaining unit 41 performs Fourier transform on the B scan interference signal from which the background data is subtracted. In this embodiment, fast Fourier transform (FFT) is employed.

In step S270, the obtaining unit 41 calculates a square of an absolute value of amplitude of the B scan interference signal subjected to the Fourier transform in step S260. A resultant value indicates an intensity of a B scan tomographic image. Specifically, the obtaining unit 41 obtains a tomographic image indicating an intensity in step S270.

In step S280, the obtaining unit 41 increments the number j of times the repeat measurement is performed indicating the number of times the B scan is repeatedly performed. In step S290, the obtaining unit 41 determines whether the number j of times the repeat measurement is performed is larger than the number m of times the repeat is performed. Specifically, the obtaining unit 41 determines whether an intensity calculation of the B scan is repeatedly performed m times in the position yi. When the number j of times the repeat measurement is performed is smaller than the number m of times the repeat is performed, the process returns to step S240 where the obtaining unit 41 repeatedly performs an intensity calculation of the B scan in the same Y position. When the number j of times the repeat measurement is performed is larger than the number m of times the repeat is performed, the process proceeds to step S300.

In step S300, the positioning unit 42 performs positioning on tomographic images for m frames of the repeat B scan in the certain Y position yi. Specifically, the positioning unit 42 selects an arbitrary one of the tomographic images for the m frames as a template. The positioning unit 42 calculates the correlation among all combinations of the tomographic images of m frames, obtains a sum of correlation coefficients for each frame, and selects a tomographic image of a frame corresponding to the largest sum as a template.

Thereafter, the positioning unit 42 compares the tomographic image selected as the template with a tomographic image in another frame so as to obtain positional shift amounts ($\delta X$, $\delta Y$, $\delta \theta$). Specifically, the positioning unit 42 calculates normalized cross-correlation (NCC) which is an index of similarity between the template image and the tomographic image of the other frame by changing a position and an angle of the template image. Then the positioning unit 42 obtains a difference between the positions of the images corresponding to a largest value of the NCC as a positional shift amount. Note that, in the present invention, any criterion may be used as the index of the similarity as long as similarity between a feature of the tomographic image selected as the template and a feature of the tomographic image of the other frame is indicated. For example, a sum of absolute difference (SAD), a sum of squared difference (SSD), zero-means normalized cross-correlation (ZNCC), phase only correlation (POC), rotation invariant phase only correlation (RIPOC), or the like may be used as the index indicating the similarity.

The positioning unit 42 performs positioning of the tomographic images for the m frames in accordance with the positional shift amounts ($\delta X$, $\delta Y$, $\delta \theta$) while applying position correction of a tomographic image indicating intensity to the tomographic images for (m−1) frames other than the template. After the positioning is completed, a process in step S310 and step S311 is performed.

In step S310, the calculation unit 43 calculates a motion contrast feature value. In this embodiment, the calculation unit 43 calculates a dispersion value for each pixel in the same position of the tomographic images for the m frames which are subjected to the positioning in step S300, and the dispersion value is determined as the motion contrast feature value. Note that various methods for obtaining the motion contrast feature value may be employed as long as an index indicates a change of a luminance value of pixels in the same Y position in a plurality of tomographic images.

On the other hand, in step S311, the calculation unit 43 calculates an average of the m tomographic images (intensity images) which are obtained in step S300 and which have been subjected to the positioning so as to generate an intensity averaging image.

In step S330, the obtaining unit 41 increments the index i of the position yi. In step S340, the obtaining unit 41 determines whether the index i is larger than the number n of measurement points. Specifically, the obtaining unit 41 determines whether the positioning, the calculation of the intensity averaging image, and the calculation of the motion contrast feature value have been performed in all the n Y positions. When the index i is equal to or smaller than the number n of the measurement positions, the process returns to step S220 whereas when the index i is larger than the number n of the measurement positions, the process proceeds to step S350 and step S360.

At a time when the process in step S340 is terminated, the intensity averaging images and 3D volume data of the motion contrast feature values of individual pixels of the tomographic images (Z-X plane) in all the Y positions have been obtained.

After the process in step S340 is terminated, the process proceeds to step S350 and step S360. A 3D blood vessel information obtaining process is executed in step S350, and a retina layer segmentation process is executed in step S360. These processes may be executed in parallel or successively executed. Note that the process in step S360 may be executed after the process in step S350 and vice versa.

First, the 3D blood vessel information obtaining process in step S350 will be described. Here, a procedure of a process of obtaining 3D blood vessel information from 3D volume data of a motion contrast feature value will be described as an example.

Figure 5:
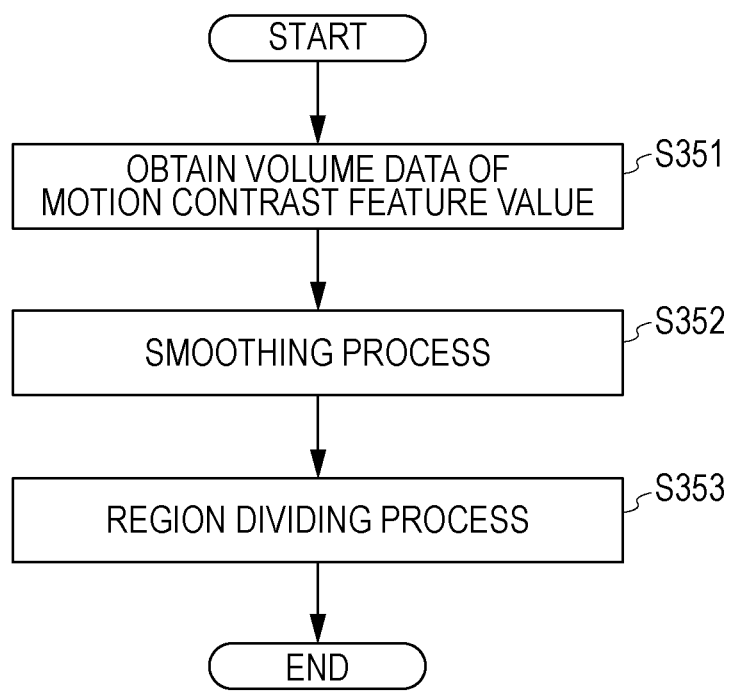
FIG. 5 is a flowchart illustrating a 3D blood vessel information obtaining process.

FIG. 5 is a flowchart illustrating the process in step S350 of FIG. 4 in detail.

In step S351, the generation unit 44 obtains the 3D volume data of the motion contrast feature value which has been obtained.

In step S352, the generation unit 44 performs a smoothing process on the 3D volume data of the motion contrast feature value so as to remove noise while blood vessel information remains.

Although the most appropriate smoothing process is changed depending on a type of the motion contrast feature value, the following smoothing process may be used, for example.

(1) Smoothing method for outputting the largest value of the motion contrast feature values from (nx×ny×nz) voxels in the vicinity of a target pixel (n is an arbitrary number).

(2) Smoothing method for outputting an average value of the motion contrast feature values in the (nx×ny×nz) voxels in the vicinity of the target pixel. A median value may be output instead of the average value.

(3) Smoothing method for weighting the motion contrast feature values in the (nx×ny×nz) voxels in the vicinity of the target pixel by corresponding distances. In this smoothing method, the larger a distance from the target pixel becomes, the lower the weighting becomes. Furthermore, since a target blood vessel intersects with a layer boundary, weighting is increased in a depth direction, for example, as the weighting method based on distances. Specifically, even if two pixels are positioned in the same distance from the target pixel, one of the pixels positioned in the depth direction is highly weighted when compared with the other of the pixels positioned in a direction orthogonal to the depth direction.

(4) Smoothing method for applying weight depending on distances and depending on differences from a pixel value of the target pixel to the motion contrast feature values in the (nx×ny×nz) voxels in the vicinity of the target pixel. The smaller the difference between pixel values becomes, the larger the weighting becomes, for example.

(5) Smoothing method for outputting a value using weighting depending on similarity between a pattern of a motion contrast feature value in a small region surrounding the target pixel and a pattern of a motion contrast feature value in a small region surrounding a peripheral pixel. In this smoothing method, the higher the similarity is, the larger the weighting is.

Note that the smoothing may be performed while blood vessel information remains. Furthermore, the smoothing process is not essential and may be omitted.

In step S353, the generation unit 44 performs the region dividing process of distinguishing a blood vessel from other regions on the 3D volume data of the motion contrast feature value which has been subjected to the smoothing process.

As the region dividing process, a method for determining a region having a voxel value indicating a motion contrast feature value equal to or smaller than a threshold value as a region other than a blood vessel, for example, may be employed. Here, an adaptive threshold setting may be performed by calculating weighted average in a mx×my×mz region in the vicinity of the target pixel and subtracting a constant number from a resultant value so that a threshold values is set for each pixel. Note that the constant number may be defined as several % of the weighted average. Furthermore, m is an arbitrary number. The threshold value may be a fixed value.

Furthermore, in the region dividing process using the threshold value, the generation unit 44 may binarize blood vessels and other regions. In this case, the generation unit 44 may perform a closing (expansion to shrinkage) process and an opening (shrinkage to expansion) process on the 3D volume data which has been subjected to the binarizing processing so as to remove noise.

Furthermore, the generation unit 44 may employ a method for determining a cost function which obtains a smallest cost when labeling is appropriately performed on regions of blood vessels and other regions and obtaining a combination of the labels corresponding to the smallest cost in the 3D volume data of the motion contrast feature value. Specifically, the generation unit 44 may employ a graph cut method, for example.

Note that other region dividing processing methods may be employed.

By the process described above, the 3D blood vessel information is obtained from the 3D volume data of the motion contrast feature value. In addition to the determination as to whether the individual pixels correspond to a blood vessel performed as described above, the number of pixels which are determined to correspond to a blood vessel and which are consecutively arranged may be taken into consideration. For example, the generation unit 44 may determine, in the pixels determined to correspond to a blood vessel, a portion in which the number of pixels determined to correspond to a blood vessel is equal to or larger than a predetermined value as a blood vessel and a portion in which the number of pixels determined to correspond to a blood vessel is smaller than the predetermined value as a portion which does not correspond to a blood vessel. Furthermore, the generation unit 44 determines continuity of the pixels determined as a blood vessel so as to detect at least one of an extending direction of the blood vessel, a length of the blood vessel, and ends of the blood vessel.

Here, as the retina layer segmentation process in step S360, a segmentation process using the intensity averaging image generated in step S311 will be described in detail.

The generation unit 44 extracts an intensity averaging image to be processed from among the intensity averaging images in the plurality of Y positions. The generation unit 44 applies a median filter and a Sobel filter to the extracted intensity averaging image so as to generate respective images (hereinafter individually referred to as a "median image" and a "Sobel image").

Subsequently, the generation unit 44 generates profiles for each A scan using the generated median image and the generated Sobel image. A profile of a luminance value is generated using the median image and a profile of gradient is generated using the Sobel image. The generation unit 44 detects a peak in the profile generated using the Sobel image. The generation unit 44 extracts a boundary (a layer boundary) between regions of the retina layer with reference to a profile of the median image corresponding to a portion before and after the peak detected in the Sobel image or a profile of the median image corresponding to a portion between peaks. Specifically, the generation unit 44 obtains layer boundary data indicating a layer boundary.

Figure 6:
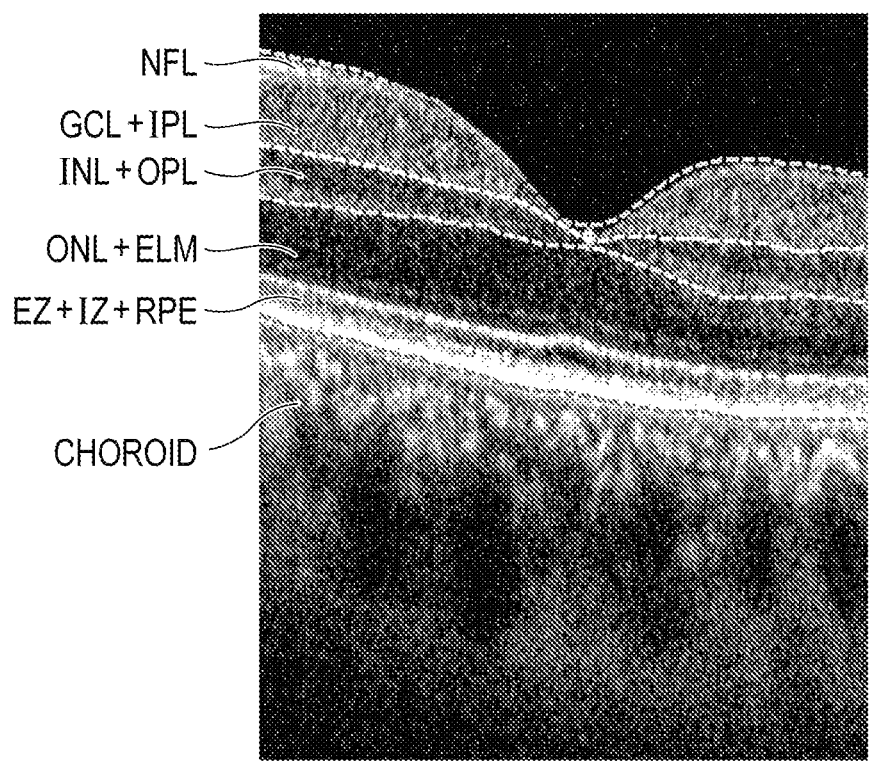
FIG. 6 is a diagram illustrating a result of segmentation.

FIG. 6 is a diagram illustrating a result of the segmentation. FIG. 6 is a diagram illustrating the intensity averaging image in the Y position, and segmentation lines (layer boundaries) denoted by dotted lines overlaid on the intensity averaging image. In the segmentation process of this embodiment, a boundary between a nerve fiber layer (NFL) and a layer of a combination of a ganglion cell layer (GCL) and an inner plexiform layer (IPL) is detected. Furthermore, a boundary between a layer of a combination of an ellipsoid zone (EZ), an interdigitation zone (IZ), and a retinal pigment epithelium (RPE) and a choroid layer and so on are detected. Note that layer boundaries to be detected are not limited to the examples described above, and the generation unit 44 may detect at least one of a boundary between a Bruch membrane and a retinal pigment epithelium layer and a boundary between the Bruch membrane and a choroid layer, for example. Note that the generation unit 44 obtains layer boundary data indicating coordinates of a detected layer boundary or the like. Specifically, the layer boundary data indicates at least one of the boundary between the Bruch membrane and the retinal pigment epithelium layer and the boundary between the Bruch membrane and the choroid layer. The generation unit 44 may obtain 3D layer boundary data by performing the process described above on the intensity averaging images in the plurality of Y positions.

The segmentation process of this embodiment is merely an example, and other methods may be employed such as a segmentation process using a Dijkstra method. Furthermore, the number of layers to be detected may be arbitrarily set.

In step S370, the determination unit 45 determines (extracts) a blood vessel which intersects with a layer boundary based on the 3D blood vessel information obtained in step S350 and the layer boundary data obtained in step S360. Specifically, the determination unit 45 determines a blood vessel which intersects with the layer boundary as a new blood vessel. Specifically, the determination unit 45 compares coordinates of the blood vessel included in the 3D blood vessel information with coordinates of the layer boundary included in the layer boundary data, for example, so as to specify the blood vessel having a coordinate the same as that of the layer boundary as a blood vessel intersecting with the layer boundary. Furthermore, in a case where a coordinate in a depth direction of the layer boundary is included between coordinates of opposite ends of the blood vessel in the depth direction obtained by the generation unit 44, the determination unit 45 may specify the blood vessel as a blood vessel intersecting with the layer boundary. The determination unit 45 may specify, in a case where a coordinate of an end of the blood vessel obtained by the generation unit 44 matches a coordinate of the layer boundary, the blood vessel as a blood vessel intersecting with the layer boundary. Specifically, the determination unit 45 determines at least one of a blood vessel intersecting with a layer boundary and a blood vessel which is in contact with the layer boundary.

Here, in a case where the 3D blood vessel information and the layer boundary are obtained from different tomographic image data, positioning is performed on the different tomographic image data so that coordinates of pixels determined as a blood vessel included in the 3D blood vessel information is compared with coordinates of the layer boundary. The positioning of the different tomographic image data is realized by positioning of integrated images obtained based on individual tomographic images corresponding to the different tomographic image data, for example. In a case where the 3D blood vessel information and the layer boundary are obtained from the same tomographic image data, the positioning described above may be omitted.

Although a blood vessel intersecting with a layer boundary is seen to be a new blood vessel in the example described above, a blood vessel, among various blood vessels, included in a predetermined range from the layer boundary may be determined as a new blood vessel. This is because a blood vessel included in the predetermined range from the layer boundary may be a new blood vessel. Although a layer boundary surface of the retina layer is uniquely determined by calculation, the boundary is fuzzy in practice, and a boundary may be broken particularly in an affected eye, and accordingly, the determination unit 45 determines whether a blood vessel is included in the predetermined range from the layer boundary surface, that is, in the vicinity of the layer boundary. The determination unit 45 determines, in a case where a coordinate of an end of the blood vessel obtained by the generation unit 44 is included in a predetermined range from the coordinate of the layer boundary, the blood vessel is determined to be included in the predetermined range from the layer boundary.

Note that the determination unit 45 may take an angle of a blood vessel into consideration so as to more reliably determine a new blood vessel. This is because a characteristic that a new blood vessel extends in a direction of a surface of the retinal is utilized. The determination unit 45 may determine a blood vessel which is positioned within the predetermined range from the layer boundary and which has an angle in a range from 45 degrees to 135 degrees relative to a horizontal direction as a new blood vessel. Note that the angle described above is merely an example, and any value may be employed as long as a blood vessel extending in the direction of the surface of the retina is extracted. The determination unit 45 may determine, as with the case described above, a new blood vessel taking an angle of a blood vessel into consideration even in the case where the blood vessel intersects with the layer boundary.

Note that the determination unit 45 may take a length of a blood vessel into consideration so as to more reliably determine a new blood vessel. This is because an inappropriate determination in which noise which is not a blood vessel is mistakenly determined as a blood vessel is to be avoided. The determination unit 45 may determine a blood vessel which is positioned within the predetermined range from the layer boundary and which has an angle in a range from 45 degrees to 135 degrees relative to a horizontal direction as a new blood vessel, for example. The determination unit 45 may determine, as with the case described above, a new blood vessel taking a length of a blood vessel into consideration even in the case where the blood vessel intersects with the layer boundary.

Note that the determination unit 45 may determine a new blood vessel taking all the positional relationship between a layer boundary and a blood vessel, and an angle of the blood vessel, and a length of the blood vessel into consideration. Furthermore, the determination unit 45 may determine a new blood vessel only based on an angle of a blood vessel. Moreover, the determination unit 45 may determine a new blood vessel based on an angle and a length of a blood vessel.

Note that the determination unit 45 may assign, to a blood vessel, reliability indicating that the blood vessel is a new blood vessel. For example, the determination unit 45 assigns higher reliability to a blood vessel intersecting with a layer boundary when compared with a blood vessel included in the predetermined range from the layer boundary. On the other hand, the determination unit 45 assigns lower reliability to a blood vessel included in the predetermined range from the layer boundary when compared with a blood vessel intersecting with the layer boundary. The assignment of the reliability is realized by setting a flag to blood vessel information based on the reliability. The determination unit 45 may assign higher reliability as a blood vessel is positioned nearer to a layer boundary. Furthermore, the determination unit 45 may assign higher reliability as an angle of a blood vessel is close to vertical. The determination unit 45 may assign higher reliability as a blood vessel is longer. Furthermore, the determination unit 45 may assign higher reliability to a blood vessel intersecting with a layer boundary when compared with a blood vessel which is in contact with the layer boundary. Furthermore, the determination unit 45 may assign higher reliability to a blood vessel intersecting with a layer boundary as the blood vessel is longer. Moreover, in a case where a blood vessel intersects with a layer boundary, the determination unit 45 may assign higher reliability to the blood vessel as the blood vessel which extends from an intersection between the layer boundary and the blood vessel toward the surface of the retina is longer. Although the reliability is assigned in the examples described above, the reliability may be replaced by a growth degree of a new blood vessel. The high reliability may be replaced by a high growth degree (large growth of a new blood vessel).

In step S380, the display controller 46 displays a blood vessel image based on the 3D blood vessel information in the display unit 70. FIG. 7 is a diagram illustrating a display screen of the display unit 70. As illustrated in FIG. 7, the display controller 46 displays a 2D blood vessel image 71, a tomographic image 72, and a 3D blood vessel image 73 in the display unit 70. Furthermore, the display controller 46 displays layer boundaries obtained by the generation unit 44 in the 3D blood vessel image 73 in an overlapping manner in the display unit 70. Specifically, the display controller 46 displays the layer boundaries indicated by the layer boundary data on the 3D blood vessel image 73 in an overlapping manner in the display unit. Note that the display controller 46 may display names of layers positioned on and below the layer boundaries so as to clearly display positions of the displayed layer boundaries.

Furthermore, the display controller 46 displays, in the display unit 70, a blood vessel determined by the determination unit 45 and other blood vessels such that the blood vessel determined by the determination unit 45 is distinguished from the other blood vessels. In the example of FIG. 7, the display controller 46 displays, in the display unit 70, arrow marks indicating blood vessels determined by the determination unit 45. Furthermore, the display controller 46 displays circles indicating portions intersecting with a layer boundary in the display unit 70. Specifically, the display controller 46 displays a blood vessel image based on 3D blood vessel data in the display unit and further displays an object indicating a blood vessel determined by the determination unit in the display unit. Here, the circles are examples of the object. A form of the object is not limited to a circle.

The display controller 46 displays the blood vessel determined by the determination unit 45 and the other blood vessels in a distinguishable manner using the arrow marks and the circles in the display unit 70. A display form indicating the blood vessel determined by the determination unit 45 is not limited to the example of FIG. 7. An end of a blood vessel included in the predetermined range from the layer boundary may be emphasized by the circle as illustrated in FIG. 7. Moreover, the display controller 46 may display the blood vessel determined by the determination unit 45 by a color different from a color of the other blood vessels in the display unit 70. The display controller 46 may display the blood vessel determined by the determination unit 45 by red and the other blood vessels by white, for example, in the display unit 70. The number of colors is not limited. Specifically, the display controller 46 displays a blood vessel image based on 3D blood vessel data in the display unit and further displays a blood vessel determined by the determination unit by a color different from a color of the other blood vessels in the display unit.

Furthermore, in a case where the reliability (or the growth degree) is assigned to a blood vessel, the display controller 46 may display the blood vessel in the display unit 70 in a display form changed depending on the reliability. For example, the display controller 46 may display a blood vessel in a color closer to red as the reliability becomes higher in the display unit 70, and display a blood vessel in a color similar to white (closer to a display color of the other blood vessels) as the reliability becomes lower.

Moreover, the display controller 46 may display blood vessels determined by the determination unit relative to all the detected layer boundaries 45 in the display unit 70 in the display form described above. Specifically, boundary data indicates a plurality of layer boundaries. Furthermore, the display controller 46 may display the blood vessel determined by the determination unit 45 relative to only an arbitrary layer boundary selected from among the plurality of layer boundaries by the user in the display unit 70 in the display form described above. Specifically, the determination unit 45 determines a blood vessel intersecting with a layer boundary selected from among the plurality of layer boundaries.

Note that the selection of a layer boundary performed by the user is realized as described below, for example. The display controller 46 displays a result of detection of a layer boundary on the tomographic image 72 in an overlapping manner in the display unit 70, and the user selects a target layer boundary from among a plurality of displayed layer boundaries by clicking, tapping, or the like. Specifically, the display controller 46 displays a 2D tomographic image based on 3D tomographic image data in the display unit and further displays the plurality of layer boundaries on the 2D tomographic image in an overlapping manner. Thereafter, in a case where one of the layer boundaries displayed on the 2D tomographic image in an overlapping manner is selected, the determination unit 45 determines a blood vessel intersecting with the layer boundary selected from among the plurality of layer boundaries.

Note that a new blood vessel intersects with the layer boundary between the choroid layer and the Bruch membrane and/or the layer boundary between the Bruch membrane and the retinal pigment epithelium layer, for example. Here, the display controller 46 may display, in the display unit 70, the blood vessel intersecting with the layer boundary between the choroid layer and the Bruch membrane and/or the layer boundary between the Bruch membrane and the retinal pigment epithelium layer in a display form different from that of the other blood vessels when the screen illustrated in FIG. 7 is entered. Specifically, in a default state of display in FIG. 7, the layer boundary between the choroid layer and the Bruch membrane and/or the layer boundary between the Bruch membrane and the retinal pigment epithelium layer may be automatically selected from among the plurality of layer boundaries.

Note that the display controller 46 may display the blood vessel determined by the determination unit 45 such that the blood vessel determined by the determination unit 45 is distinguished from the other blood vessels. Furthermore, the display controller 46 may display a fundus image in the display unit 70, and display arrow marks, circles, and the like indicating a position of a blood vessel of the fundus determined by the determination unit 45 in an overlapping manner. Note that the fundus image may be obtained by integrating tomographic images or obtained by a fundus camera or the SLO. Positioning of the 3D blood vessel image and the fundus image is realized by positioning of an integrated image obtained from the tomographic image data which is a base of the 3D blood vessel image and the fundus image. Specifically, positioning of the 3D blood vessel image and the fundus image is performed using the tomographic image data. Accordingly, the display controller 46 may display the arrow marks, the circles, and the like indicating a position of the blood vessel determined by the determination unit 45 on the fundus image in an overlapping manner in the display unit 70.

Note that the display controller 46 may not display all the 2D blood vessel image 71, the tomographic image 72, and the 3D blood vessel image 73 in the display unit 70 and may display an arbitrary image or arbitrary images in the display unit 70. For example, the display controller 46 may display only the 3D blood vessel image 73 on which the layer boundaries are superposed in the display unit 70 in a state in which the blood vessel determined by the determination unit 45 is distinguished from the other blood vessels.

As described above, according to this embodiment, a blood vessel which is a possible new blood vessel may be specified. Furthermore, the blood vessel determined as the new blood vessel is displayed such that the new blood vessel is distinguished from the other blood vessels so that the user, such as a doctor, may easily and swiftly recognize the blood vessel which is a possible new blood vessel. Furthermore, in a default state in which blood vessel images are displayed, a blood vessel intersecting with the layer boundary between the choroid layer and the Bruch membrane and/or the layer boundary between the Bruch membrane and the retinal pigment epithelium layer where a new blood vessel is highly likely to be generated are displayed in a state in which the blood vessel is distinguished from the other blood vessels. Accordingly, the user, such as a doctor, may swiftly recognize the blood vessel which is a possible new blood vessel.

Furthermore, according to this embodiment, a blood vessel is displayed in the display form based on reliability, and therefore, this display assists a determination as to whether the blood vessel is actually a new blood vessel made by the user, such as a doctor. Furthermore, according to this embodiment, a blood vessel is displayed in the display form based on a growth degree, and therefore, the user, such as a doctor, may swiftly recognize a degree of disease with ease.

Furthermore, according to this embodiment, 3D blood vessel image and a layer boundary are obtained based on the same tomographic image data, and therefore, the positional relationship between the 3D blood vessel image and the layer boundary may be easily recognized.

Although 3D layer boundary data and 3D blood vessel data are obtained based on the same tomographic image data according to this embodiment, the present invention is not limited to this. A plurality of tomographic image data indicating the layers of the fundus to be used in the generation of 3D blood vessel data may be different from a plurality of tomographic image data indicating the layers of the fundus included in the 3D tomographic image data to be used in an obtainment of layer boundary data. Furthermore, angles of view of the plurality of tomographic image data indicating the layers of the fundus to be used in generation of the 3D blood vessel data may be smaller than those of the plurality of tomographic image data indicating the layers of the fundus included in the 3D tomographic image data to be used in an obtainment of the layer boundary data. Specifically, the tomographic image data for obtaining the 3D layer boundary data may have an angle of view larger than that of the tomographic image data in the foregoing embodiment so that the user, such as a doctor, determines a range in the fundus to obtain the 3D blood vessel data.

Note that the scanning performed a plurality of times in substantially the same position is not required when tomographic image data having a large angle of field is to be obtained. In a case where the tomographic image data of large angle of field is obtained, the generation unit 44 may obtain 3D layer boundary data from the tomographic image data of the large angle of view. Specifically, the 3D layer boundary data may be obtained from tomographic image data different from tomographic image data from which 3D blood vessel data is obtained.

Although the 3D blood vessel data and the 3D layer boundary data are used in the foregoing embodiments, the present invention is not limited to this and 2D blood vessel data and 2D layer boundary data may be used. Even if the 2D data is used, a blood vessel intersecting with a layer boundary may be specified, and accordingly, the same effect of the foregoing embodiment may be attained.

Second Embodiment

Configuration of Entire Imaging Apparatus

A case where a polarization OCT is used will be described in a second embodiment. According to the polarization OCT, a tomographic image from which a retinal pigment epithelium layer which cancels polarization may be easily extracted may be obtained. Therefore, in this embodiment, the ophthalmic apparatus detects a layer boundary between the retinal pigment epithelium layer and a Bruch membrane or the like and determines a blood vessel and the like which intersects with the detected layer boundary as a new blood vessel. Specifically, this embodiment is different from the first embodiment in a method for detecting a layer boundary. Note that a scanning pattern and so on which are not particularly mentioned are the same as those of the first embodiment, and descriptions thereof are omitted.

Figure 8:
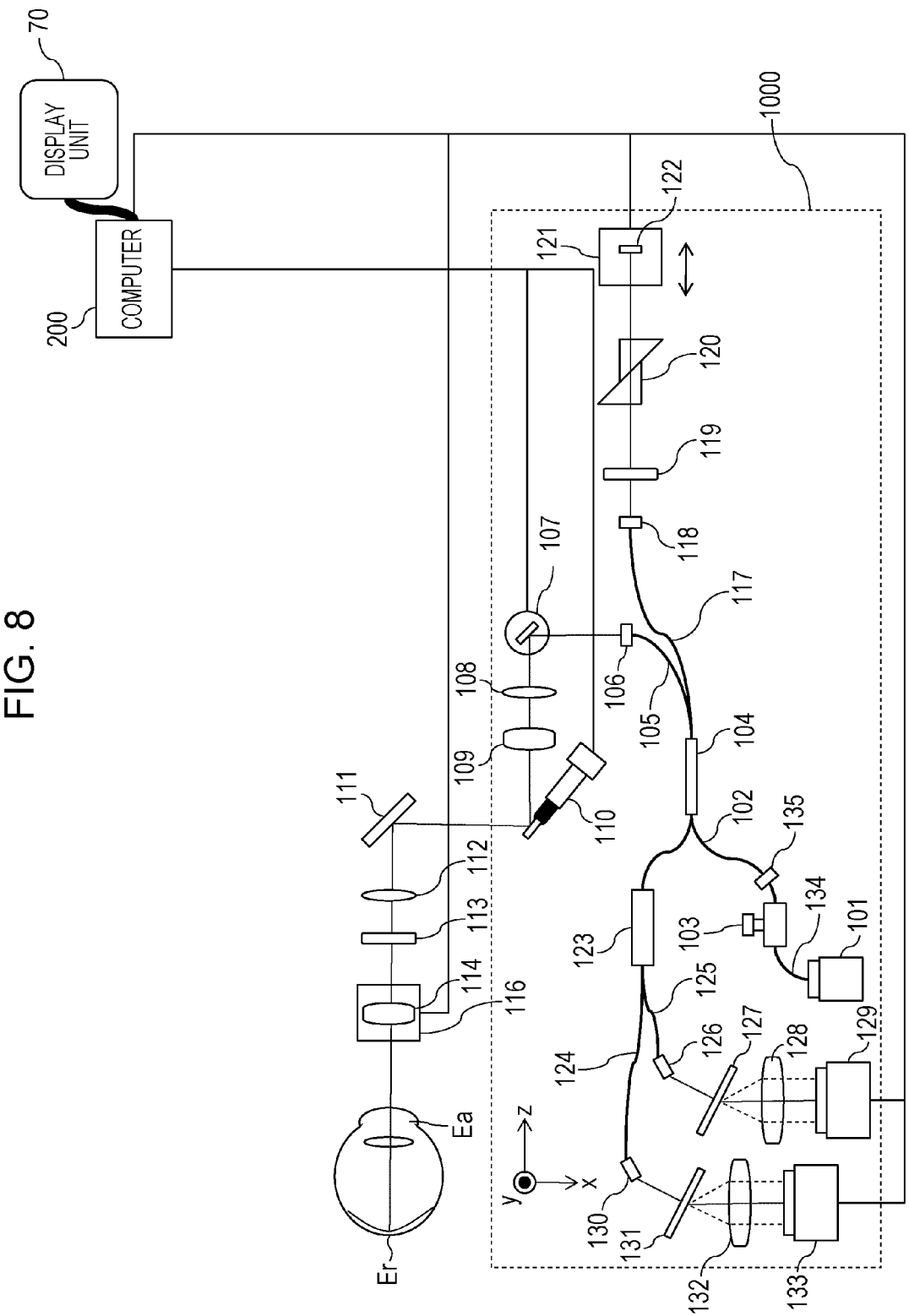
FIG. 8 is a diagram illustrating a configuration of polarization OCT.

FIG. 8 is a diagram illustrating the ophthalmic apparatus according to this embodiment.

The ophthalmic apparatus includes polarization sensitive OCT (PS-OCT) 1000 and a computer 200. Note that the computer 200 is substantially the same as the computer 40 of the first embodiment except for some functions. Specifically, 3D tomographic image data is obtained by the PS-OCT 1000.

Configuration of PS-OCT 1000

A configuration of the PS-OCT 1000 will be described.

A light source 101 is an super luminescent diode (SLD) light source which is a low coherent light source, and emits light having a central wavelength of 850 nm and a bandwidth of 50 nm, for example. Although the SLD is used as the light source 101, any light source may be used as long as low coherent light is emitted, such as an amplified spontaneous emission (ASE) light source.

The light emitted from the light source 101 is transmitted through a single mode (SM) fiber 134, a polarization controller 103, a connector 135, and a polarization maintaining (PM) fiber 102. The light emitted from the light source 101 is further guided to a fiber coupler 104 having a polarization maintaining function which divides the light into measurement light (or OCT measurement light) and reference light (or reference light corresponding to the OCT measurement light).

The polarization controller 103 controls a state of polarization of the light emitted from the light source 101 so as to obtain linearly polarized light. A division rate of the fiber coupler 104 is 90 (reference light) to 10 (measurement light).

The divided measurement light is transmitted through a PM fiber 105 and emitted from a collimator 106 as parallel light. The emitted measurement light is transmitted through an X scanner 107 configured by a Galvano mirror which scans the measurement light in a horizontal direction in a fundus Er, a lens 108, and a lens 109. Furthermore, the emitted measurement light is transmitted through a Y scanner 110 configured by a Galvano mirror which performs scanning using the measurement light in a vertical direction in the fundus Er to a dichroic mirror 111. The X scanner 107 and the Y scanner 110 are controlled by an obtaining unit 41 and may scan a desired range of the fundus Er (a range in which a tomographic image is to be obtained, a position where a tomographic image is to be obtained, or a position emitted by the measurement light) with the measurement light. The dichroic mirror 111 has a characteristic in which light having a wavelength of 800 nm to 900 nm is reflected and other light is transmitted.

The measurement light reflected by the dichroic mirror 111 is transmitted through a lens 112 and a λ/4 polarizing plate 113 (an example of a polarization control member) which is disposed with an inclination of 45 degrees in an in-plane which is vertical to an optical axis of the measurement light so that a phase of the measurement light is shifted by 90 degrees, and accordingly, polarization control is performed so that circularly polarized light is obtained. Note that the inclination of the λ/4 polarizing plate 113 preferably has an angle (an example of an arrangement state) corresponding to an inclination relative to an optical axis of a polarization division plane of a fiber coupler 123 incorporating a polarizing beam splitter, for example.

Note that the λ/4 polarizing plate 113 is preferably detachable from a light path. For example, a mechanical configuration in which an axis which is parallel to an optical axis is used as a rotation axis for rotation of the λ/4 polarizing plate 113 may be employed. By this, a small apparatus capable of easily performing switching between an SLO optical system and a PS-SLO optical system may be realized. Furthermore, a small apparatus capable of easily performing switching between an OCT optical system and a PS-OCT optical system may be realized.

Although light to be incident on an eye to be inspected is subjected to the polarization control by the λ/4 polarizing plate 113 which is disposed on the in-plane which is vertical to the optical axis of the measurement light in a state in which the λ/4 polarizing plate 113 is inclined by 45 degrees so that circularly polarized light is obtained, the circularly polarized light may not be obtained in the fundus Er due to a characteristic of the eye to be inspected. Therefore, the obtaining unit 41 may finely control the inclination of the λ/4 polarizing plate 113.

The measurement light which has been subjected to the polarization control so as to be changed to the circular polarized light is focused on a retina layer of the fundus Er through an anterior eye portion Ea of the eye to be inspected by a focus lens 114 mounted on a stage 116. The measurement light emitted to the fundus Er is reflected and scattered in various retina layers and returns to the fiber coupler 104 through the optical path described above.

On the other hand, the reference light divided by the fiber coupler 104 is transmitted through a PM fiber 117 and emitted from a collimator 118 as parallel light. As with the measurement light, the emitted reference light is subjected to polarization control by a λ/4 polarizing plate 119 which is disposed in a plane vertical to an optical axis of the reference light and which is inclined from P polarized light to S polarized light by 22.5 degrees. The reference light is transmitted through a dispersion compensation glass 120, reflected by a mirror 122 on a coherence gate stage 121, and returns to the fiber coupler 104. Since the reference light passes the λ/4 polarizing plate 119 twice, linearly polarized light is returns to the fiber coupler 104.

The coherence gate stage 121 is controlled by a driving controller so as to cope with uniqueness of an axial length of the eye to be inspected.

The measurement light and the reference light which have returned to the fiber coupler 104 are combined with each other so that interference light is obtained which is to be incident on the fiber coupler 123 incorporating the polarizing beam splitter and which is divided into light beams in different polarization directions (P polarized light and S polarized light in this embodiment) by a division rate of 50:50.

The P polarized light is transmitted through a PM fiber 124 and a collimator 130, divided by a grating 131, and received by a lens 132 and a line camera 133. Similarly, the S polarized light is transmitted through a PM fiber 125 and a collimator 126, divided by a grating 127, and received by a lens 128 and a line camera 129. Note that the gratings 127 and 131 and the line cameras 129 and 133 are disposed so as to correspond to the individual polarization directions.

The light beams received by the line cameras 129 and 133 are output as electric signals corresponding to light intensities, and the output electric signals are obtained by the obtaining unit 41.

Although the λ/4 polarizing plate 113 controls inclination using the polarizing beam splitter as a reference, the inclination may be controlled relative to a straight line which connects a center of an optic disk to a center of a macula in a fundus. The same effect may be attained in a case where the polarizing beam splitter and the λ/4 polarizing plates 113 and 119 are controlled using a vertical direction as a polarization reference.

Computer 200

The computer 200 of this embodiment is substantially the same as the computer 40, and therefore, a detailed description thereof is omitted.

Image Processing

Next, a signal processing method in polarization OCT will be described. In terms of segmentation of a retina layer, B scan is performed only once on the same portion, and therefore, repetitive scan is not particularly described hereinafter. However, to obtain 3D blood vessel information, a motion contrast feature value is required to be obtained, and therefore, B scan is required to be performed a plurality of times also in the second embodiment.

Generation of Tomographic Image and Generation of Fundus Image

The obtaining unit 41 performs reconstruction processing employed in general spectral domain OCTs (SD-OCTs) on the interference signals output from the line cameras 129 and 133. Then the obtaining unit 41 generates two tomographic images based on polarization components (that is, a tomographic image based on first polarized light and a tomographic image based on second polarized light).

First, the obtaining unit 41 performs fixed pattern noise reduction on an interference signal. In the fixed pattern noise reduction, pattern noise is extracted by averaging a plurality of detected A scan signals and subtracting the fixed pattern noise from the input interference signal.

Subsequently, the obtaining unit 41 converts a wavelength of the interference signal into a wavenumber and performs Fourier transform so as to generate a tomographic signal (or a tomographic signal indicating a polarization state).

By performing the process described above on the interference signals of the two polarization components, two tomographic images are generated.

Generation of Luminance Image

The obtaining unit 41 generates tomographic images indicating intensities (hereinafter referred to as "luminance images" where appropriate in this embodiment) using the two tomographic signals described above.

The luminance image is basically the same as a tomographic image of general OCTs, and a pixel value r is calculated in accordance with Expression 4 using tomographic signals $A_H$ and $A_V$ obtained by the line cameras 129 and 133.

$$r = \sqrt{A_H^2 + A_V^2} \qquad \text{Expression 4}$$

In this embodiment, as with the first embodiment, the generation unit 44 obtains 3D blood vessel information based on a tomographic image indicating an intensity obtained in accordance with Expression 4.

Generation of DOPU Image

The obtaining unit 41 calculates a Stokes's vector S for each pixel in accordance with Expression 5 using the obtained tomographic signals $A_H$ and $A_V$ and a phase difference $\Delta\phi$ between the tomographic signals $A_H$ and $A_V$.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \qquad \text{Expression 5}$$

Note that Δϕ is calculated as "$\Delta\phi=\phi_V-\phi_H$" using the phases $\phi_H$ and $\phi_V$ of the signals obtained when the two tomographic images are calculated.

Subsequently, the obtaining unit 41 sets a window having a length of approximately 70 μm in a main scanning direction of the measurement light and a depth of approximately 18 μm in a depth direction on B scan images. Then the obtaining unit 41 averages elements of the Stokes's vector calculated for each pixel in accordance with Expression 5 in the individual windows and degrees of polarization uniformity (polarization uniformity DOPU) in the windows are calculated in accordance with Expression 6.

$$DOPU=\sqrt{Q_m^2+U_m^2+V_m^2} \quad \text{Expression 6}$$

Note that $Q_m$, $U_m$, and $V_m$ are values obtained by averaging elements Q, U, and V of Stokes's vectors in the windows, respectively. When this process is performed on all the windows of the B scan image, a DOPU image (or a tomographic image indicating polarization uniformity) is generated.

The DOPU is a numerical value indicating the polarization uniformity, and the numerical value is nearly 1 in a portion in which polarization is maintained and is smaller than 1 in a portion in which polarization is cancelled, that is, not maintained. A structure of a retina has a characteristic in which a retinal pigment epithelium layer cancels a polarization state, and therefore, a portion corresponding to the retinal pigment epithelium layer in the DOPU image has the numerical value smaller than those of other regions. The DOPU image is obtained by imaging a layer which cancels polarization, such as the retinal pigment epithelium layer, and accordingly, even in a case where the retinal pigment epithelium layer is deformed due to disease or the like, the RPE may be more reliably imaged when compared with a change of luminance.

The generation unit 44 obtains segmentation information of the RPE from the DOPU image obtained by the obtaining unit 41. Specifically, a value of the DOPU of the portion corresponding to the retinal pigment epithelium layer is smaller than those of the other regions as described above, and therefore, the generation unit 44 extracts a region having the small DOPU value as the retinal pigment epithelium layer. Then the generation unit 44 may extract a lower end of the extracted retinal pigment epithelium layer as a layer boundary between the retinal pigment epithelium layer and the Bruch membrane.

A method for determining a new blood vessel employed in the display controller 46 is the same as that of the first embodiment, and therefore, a description of a process performed by the display controller 46 is omitted.

According to this embodiment, the layer boundary between the retinal pigment epithelium layer and the Bruch membrane may be easily detected by PSOCT, and therefore, a blood vessel which intersects with the layer boundary between the retinal pigment epithelium layer and the Bruch membrane and a blood vessel in the vicinity of the layer boundary may be easily determined. In particular, a new blood vessel is likely to intersect with the layer boundary between the retinal pigment epithelium layer and the Bruch membrane, and therefore, the PSOCT is effectively used to specify a blood vessel which is a possible new blood vessel.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-168287, filed Aug. 27, 2015, which is hereby incorporated by reference herein in its entirety.

What is claimed is:

1. An ophthalmic apparatus comprising:
   a generation unit configured to generate 3D blood vessel data indicating a blood vessel in a fundus based on a plurality of tomographic image data indicating cross sections of the fundus;
   a boundary obtaining unit configured to obtain layer boundary data indicating at least one layer boundary based on 3D tomographic image data including the plurality of tomographic image data indicating the cross sections of the fundus, wherein the layer boundary data indicates at least one of a boundary between a Bruch membrane and a retinal pigment epithelium layer and a boundary between the Bruch membrane and a choroid layer; and
   a determination unit configured to determine a blood vessel intersecting with the layer boundary by comparing the 3D blood vessel data with the layer boundary data.

2. The ophthalmic apparatus according to claim 1, further comprising a display controller configured to cause a display unit to display at least one of a 3D blood vessel image indicated by the 3D blood vessel data and a 2D blood vessel image obtained by integrating the 3D blood vessel data in a depth direction of the fundus, and to cause the display unit to display a blood vessel determined by the determination unit in a state in which the blood vessel determined by the determination unit is distinguished from other blood vessels.

3. The ophthalmic apparatus according to claim 1, wherein the boundary obtaining unit obtains layer boundary data indicating at least one layer boundary based on the 3D tomographic image data including a plurality of tomographic image data indicating cross sections of the fundus to be used in generation of the 3D blood vessel data.

4. The ophthalmic apparatus according to claim 2, wherein the display controller causes the display unit to display layer boundaries indicated by the layer boundary data which are superposed on the 3D blood vessel image.

5. The ophthalmic apparatus according to claim 1, wherein a plurality of tomographic image data indicating cross sections of the fundus to be used in generation of the 3D blood vessel data is different from a plurality of tomographic image data indicating cross sections of the fundus included in the 3D tomographic image data, and angles of field of the plurality of tomographic image data indicating the cross sections of the fundus to be used in generation of the 3D blood vessel data are smaller than angles of field of the plurality of tomographic image data indicating the cross sections of the fundus included in the 3D tomographic image data.

6. The ophthalmic apparatus according to claim 1, wherein the layer boundary data indicates a plurality of layer boundaries, and the determination unit determines a blood vessel intersecting with a layer boundary selected from among the plurality of layer boundaries.

7. The ophthalmic apparatus according to claim 6, wherein the display controller displays a 2D tomographic image based on the 3D tomographic image data in the display unit and the plurality of layer boundaries superposed on the 2D tomographic image, and the determination unit determines, in a case where the layer boundary displayed in a state in which the layer boundary is superposed on the 2D tomographic image is selected, a blood vessel intersecting with the layer boundary selected from among the plurality of layer boundaries.

8. The ophthalmic apparatus according to claim 1, further comprising a display controller configured to cause a display unit to display a blood vessel image based on the 3D blood vessel data and cause the display unit to display the blood vessel determined by the determination unit in a color different from a color of other blood vessels.

9. The ophthalmic apparatus according to claim 1, wherein a blood vessel image based on the 3D blood vessel data is displayed in a display unit and an object indicating a blood vessel determined by the determination unit is displayed in the display unit.

10. The ophthalmic apparatus according to claim 8, wherein the 3D tomographic image data is obtained by polarization sensitive optical coherence tomography.

11. An information processing method comprising:
generating 3D blood vessel data indicating a blood vessel in a fundus based on a plurality of tomographic image data indicating cross sections of the fundus;
obtaining layer boundary data indicating at least one layer boundary based on 3D tomographic image data including the plurality of tomographic image data indicating the cross sections of the fundus, wherein the layer boundary data indicates at least one of a boundary between a Bruch membrane and a retinal pigment epithelium layer and a boundary between the Bruch membrane and a choroid layer; and
determining a blood vessel intersecting with the layer boundary by comparing the 3D blood vessel data with the layer boundary data.

12. A non-transitory storage medium storing a program which causes a computer to execute the information processing method set forth in claim 11.

13. An ophthalmic apparatus comprising:
a generation unit configured to generate blood vessel data indicating a blood vessel in a fundus based on a plurality of tomographic image data indicating cross sections of the fundus;
a boundary obtaining unit configured to obtain layer boundary data indicating at least one layer boundary based on the tomographic image data indicating the cross sections of the fundus, wherein the layer boundary data indicates at least one of a boundary between a Bruch membrane and a retinal pigment epithelium layer and a boundary between the Bruch membrane and a choroid layer; and
a determination unit configured to determine a blood vessel intersecting with the layer boundary by comparing the blood vessel data with the layer boundary data.

14. An ophthalmic apparatus comprising:
a generation unit configured to generate 3D blood vessel data indicating a blood vessel in a fundus based on a plurality of tomographic image data indicating cross sections of the fundus;
a boundary obtaining unit configured to obtain layer boundary data indicating at least one layer boundary based on 3D tomographic image data including the plurality of tomographic image data indicating the cross sections of the fundus, wherein the layer boundary data indicates at least one of a boundary between a Bruch membrane and a retinal pigment epithelium layer and a boundary between the Bruch membrane and a choroid layer; and
a display controller configured to cause a display unit to display layer boundaries indicated by the layer boundary data which are superposed on a 3D blood vessel image indicated by the 3D blood vessel data.

* * * * *